United States Patent [19]
Ohsawa et al.

[11] Patent Number: 5,174,894
[45] Date of Patent: Dec. 29, 1992

[54] BLOOD COMPONENT SEPARATION APPARATUS

[75] Inventors: Takaaki Ohsawa; Tatsuya Fujii, both of Fuji, Japan

[73] Assignee: Terumo Kabushiki Kaisha, Tokyo, Japan

[21] Appl. No.: 449,914

[22] PCT Filed: Jun. 25, 1988

[86] PCT No.: PCT/JP88/00633
  § 371 Date: Dec. 21, 1989
  § 102(e) Date: Dec. 21, 1989

[87] PCT Pub. No.: WO88/10125
  PCT Pub. Date: Dec. 29, 1988

[30] Foreign Application Priority Data
Jun. 25, 1987 [JP] Japan ................. 62-158141

[51] Int. Cl.⁵ .............. B01D 63/08; B01D 61/18
[52] U.S. Cl. .......................... 210/86; 210/85;
  210/90; 210/206; 210/321.6; 210/321.84; 604/6
[58] Field of Search ............... 210/85, 86, 90, 94,
  210/97, 103, 104, 130, 136, 198.1, 206, 321.6,
  321.75, 321.84; 604/4-6

[56] References Cited

U.S. PATENT DOCUMENTS

| | | | |
|---|---|---|---|
| 3,520,803 | 7/1970 | Iaconelli | 210/321.75 X |
| 3,774,762 | 11/1973 | Lichtenstein | 210/929 X |
| 3,912,455 | 10/1925 | Lichtenstein | 422/61 |
| 3,946,731 | 3/1976 | Lichtenstein | 210/929 |
| 4,436,620 | 3/1984 | Bellotti et al. | 210/90 |
| 4,479,762 | 10/1984 | Bilstad et al. | 417/395 |
| 4,610,781 | 9/1986 | Bilstad et al. | 210/85 |
| 4,661,246 | 4/1987 | Ash | 210/94 |

FOREIGN PATENT DOCUMENTS

| | | |
|---|---|---|
| 2242994 | 4/1975 | France . |
| 2513884 | 4/1983 | France . |
| 2570948 | 4/1986 | France . |
| 60-500159 | 2/1985 | Japan . |
| 60-190967 | 9/1985 | Japan . |
| 2110564 | 6/1983 | United Kingdom . |

OTHER PUBLICATIONS

American Society for Artificial Internal Organs, vol. 32, No. 1 Jul/Sep. 1986, pp. 4–5–409; Yamazaki et al.; "An Automated Plasma Collector with Innovative Membrane and Cassette-Like Disposable Set".

*Primary Examiner*—W. Gary Jones
*Attorney, Agent, or Firm*—Frishauf, Holtz, Goodman & Woodward

[57] ABSTRACT

A blood component separation apparatus is disclosed which comprises at least three plate-like members arranged in a stacked fashion, a blood circulation circuit composed of at least two layers which are arranged between the associated plate-like members, a filter for blood component separation which is incorporated into a blood passage, a plurality of connection ports provided in the plate-like members to allow them to communicate with the blood circulation circuit, communication tubes mounted in the blood circulation circuit to place part of the connection ports in communication with an associated connection port, the communication tube being adapted to control a fluid communication in the blood circulation circuit and an external function section connected to corresponding connection ports. According to the present invention, a three-dimensional blood circuit of a multi-layered structure can be provided which can build up a complex blood circuit of a better function than that of a conventional flat blood circulation circuit.

24 Claims, 5 Drawing Sheets

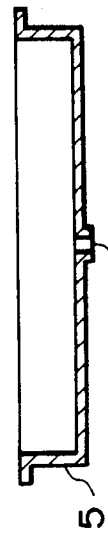
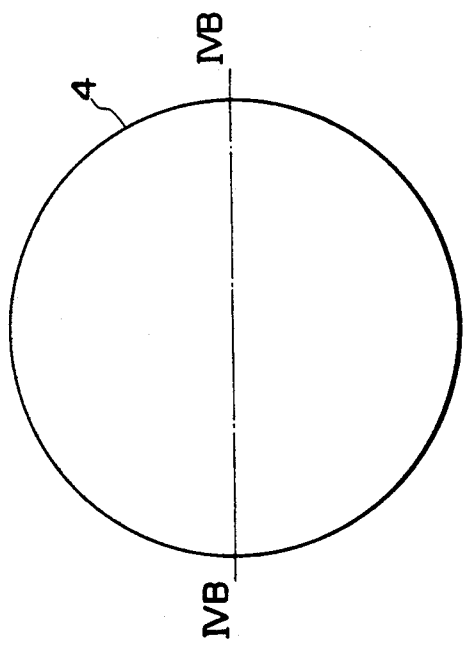
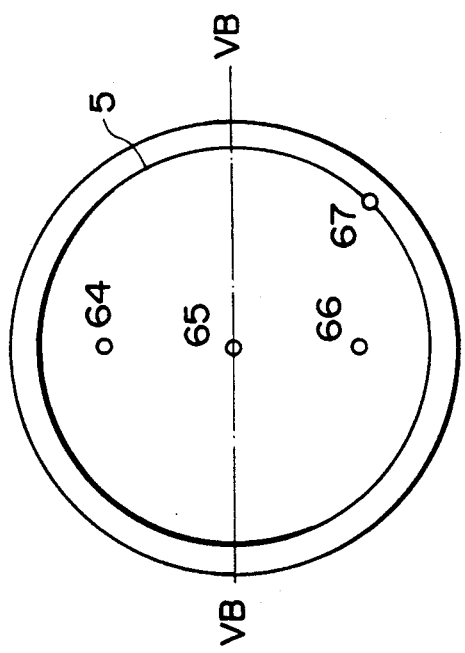

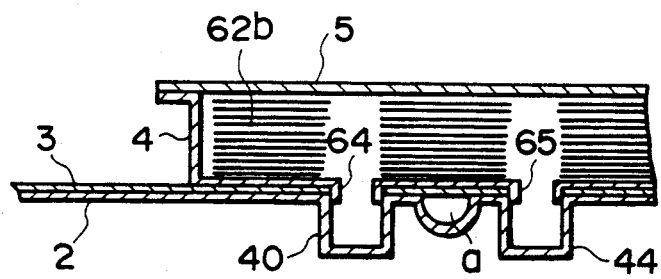
F I G. 6
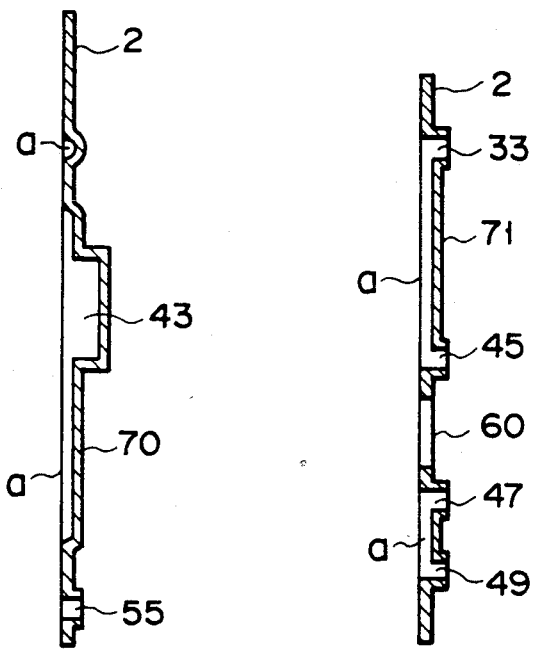
F I G. 7   F I G. 8
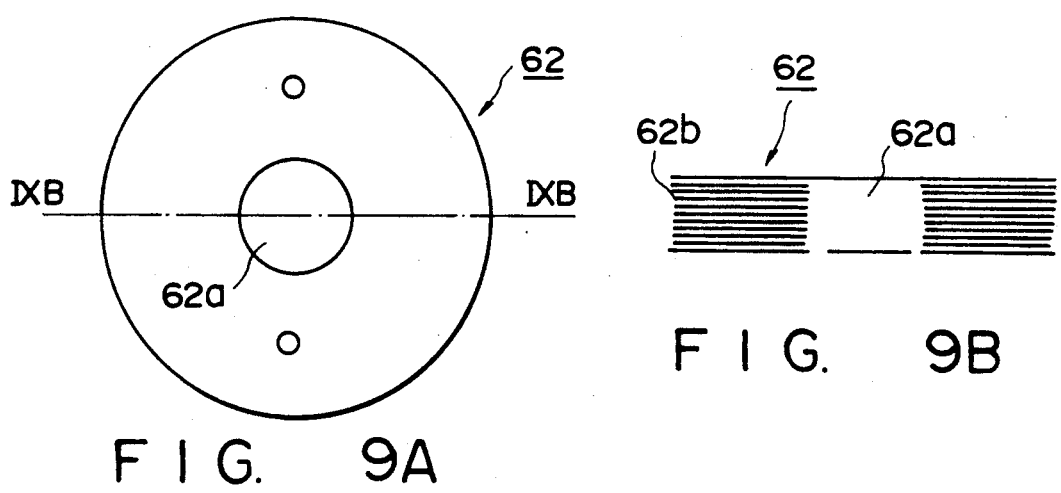
F I G. 9A   F I G. 9B

BLOOD COMPONENT SEPARATION APPARATUS

TECHNICAL FIELD

The present invention relates to an apparatus for separating a blood component and, in particular, a blood component separation apparatus which can build up a blood circulation circuit of a multi-layered structure integral with a blood component separator.

BACKGROUND ART

The blood component separation apparatus is adapted to a separate various components from the blood, such as a blood corpuscle component and blood plasma component. The apparatus comprises a separator equipped with a filter for separating a given component from the blood and a blood circuit section which allows the blood to be extracorporeally circulated at a given sequence including the separator and returns it back thereto. The blood circulation circuit is generally composed of:

(1) An inlet-side circuit for supplying the blood which has collected from the donor to the separator;

(2) An outlet-side circuit for returning the blood whose component, such as the blood plasma, has been separated by means of the separator back to the donor; and (3) A treatment circuit (called as a filtrate circuit for blood plasma separation) for treating a component, such as the blood plasma, which has been separated by means of the separator.

Further, the respective blood circuit includes a pressure monitoring circuit, tubes for a blood pump, a liquid medicine inlet, a bubble trap, and so on, so as to allow the circulation of the blood, the smooth filtration of it by the separator, and so on.

Upon the assembly of a blood component separation apparatus, the aforementioned blood circuits and function section are placed in proper locations and have all to be connected together exactly. The assembling operations are very complex in nature and there is a risk that a connection error will occur oftener.

In order to alleviate cumbersome operations upon assembly and to avoid the aforementioned connection error, a blood plasma separation apparatus has been proposed, for example, in Japanese Patent Disclosure (KOKAI) No. 60-190967, which is composed of a blood circuit and intra-circuit function section alone as has already been set forth above and is connected to a hollow-fiber type blood separation filter. In this apparatus, the blood circuit is composed of two plate-like members stacked with a grooved passage defined by at least one of them to provide a stacked structure.

Japanese Patent Disclosure (KOKAI) No. 60-500159 discloses a blood plasma separation apparatus which incorporates not only a blood circuit and function section as have been set out above, but also a hollow-fiber type blood plasma separation filter, in the same casing to provide a packaged unit and which drives the blood under air pressure control. This apparatus is all of a flat array type including the blood circuit, the blood plasma separation filter and the other function section.

The recent advance of the blood component separation technique in this field permits a high-level separation of the blood plasma by, for example, a double filtration method or a single-needle type recirculation blood plasma collection method. The double filtration method is directed to separating a protein of a large molecular weight from the blood. On the other hand, the single needle type recirculation blood plasma collection method permits the human blood to be collected out of, and returned back to, the donor by the single syringe needle in which case, in order to draw as large an amount of blood plasma as possible from the blood, plasma-separated blood is recirculated to the separation filter through the utilization of a blood storage container, a recirculation circuit and a recirculation pump.

The aforementioned blood component separation apparatus requires a complicated blood circulation circuit and a more cumbersome assembling operation. In the case of such a blood component separation apparatus including the aforementioned blood circuit, the function section and the separator as an integral unit, a current demand cannot be satisfied because these component parts have to be arranged as a flat array unit.

DISCLOSURE OF INVENTION

An object of the present invention is to provide a blood component separation apparatus which can be applied to a system needing a very complex circuit arrangement and multi-function section, such as a single needle type recirculation blood plasma collection system or a double filtration system, and can do so by a simpler assembling operation without involving any connection error.

Another object of the present invention is to provide a blood component separation apparatus which, upon the use of it, can simplify a requisite preparation operation following the extacorporeal circulation of the blood.

In order to achieve the aforementioned object, according to the present invention, a blood circuit for allowing the extacorporeal circulation of the blood, intra-circuit multi-function section and separation filter are three-dimensionally assembled, as an integral unit, in the same casing. Further, external connection ports for communicating with an internal blood circuit are provided in the casing to allow the external function port to communicate with an associated external connection port or another circulation line.

That is, the blood component separation apparatus of the present invention comprises at least three plate-like members arranged in a stacked fashion, a blood circulation circuit composed of at least two layers which are arranged between the associated plate-like members, a filter for blood component separation which is incorporated in the blood passage, a plurality of connection ports mounted in the plate-like members to allow them to communicate with the blood circulation circuit, communication tubes mounted in the blood circulation circuit to place part of the connection port in communication with the associated connection port, the communication tube being adapted to control a fluid communication in the blood circulation circuit, and an external function section connected to other associated port.

According to the present invention, as the plate-like members, use can be made of plates which are molded of synthetic resin. In this case, grooves and recesses for defining a blood circulation circuit, as well as through-holes for associated connection ports, are provided in the plates. That is, a blood circulation circuit is defined between the plate-like members by stacking the plate-like members in a mating fashion. According to the present invention, at least three plate-like members are stacked in a mating fashion to provide a three-dimensional blood circuit, an important feature of the present invention. That is, the blood circuit is three-dimensionally formed to enable a blood circuit to be achieved in a more complicated way than the conventional counterpart which is simply of a flat array type.

According to the present invention, the blood circulation circuit contains a casing which has a blood component separation filter incorporated therein. As the filter which is contained in the casing, use may usually be made of a microporous membrane having a pore size of 0.005 to 20 μm. For a double filtration method using a complicated circuit, or a single needle type recirculation blood plasma collection method, the microporous membrane has a pore size of 0.1 to 1 μm. A hollow fiber- and a flat layer-type filter may also be employed. However, the flat layer-type filter is preferred to the hollow fiber type filter which requires a potting process.

The aforementioned blood circulation circuit contains a bubble trap, a pressure monitoring circuit, a liquid level detection section for detecting the level of a liquid such as the blood or physiological saline, a hemolysis detection section for detecting the hemoglobin level in the blood, a blood storage container, a sampling inlet for sampling the blood or blood component, and so on.

According to the present invention, a soft communication tube is generally used to connect the connection port to the associated connection port. The connection tube, if being properly set relative to an external device such as a roller pump or circuit clamp, serves as a pump tube or circuit blocking means. It is possible to mount, for example, the roller pump and circuit clamp as a structure integral with the plate-like member.

According to the present invention, examples of the external function section connected to the connection ports are as follows:

(a) a blood sampling passage line, including a syringe needle for blood sampling or catheter;

(b) a blood return passage line for returning the blood back to the donor;

(c) an anti-coagulant mixing passage line for mixing an anti-coagulant such as an ACD (acid citrate dextrose), CPD (citrate phosphate dextrose), heparin and mesylated gabexate, into the blood sampled;

(d) a pressure monitoring port connection passage line for monitoring a pressure in respective portion of the extracorporeal circulation circuit;

(e) a physiological saline passage line for washing the interior of the extracorporeal circulation circuit, which is connected to a physiological saline container;

(f) an anti-coagulant container connection passage line connected to the anti-coagulant container;

(g) a blood component sampling passage line connected to the container for storing a blood component, such as the platelet and plasma, which is separated from the blood;

(h) various passage lines connected, as required, to the associated containers, for example, one for a potassium preparation to be used for a citric acid-based drug application and one for a frozen fresh blood plasma to be used upon the replacement of the blood plasma or one for an albumin preparation;

(i) a blood storage container for temporarily storing the sampled blood or the filtered blood;

(j) a spent liquid storage container for discharging a circuit washing liquid, a blood priming liquid, and so on;

(k) a blood component-separated container for discharging the blood component, such as the lean protein plasma separated from the filter or a rich protein plasma of a high molecular weight, or other containers.

As has been set forth above, the blood component separation apparatus of the present invention is composed of a specific blood circuit of a three-dimensional layered structure with a filtering mechanism incorporated therein. It is thus possible to readily form a complicated blood circuit of a multi-layered structure which has not been able to be readily achieved in the conventional technique. It is also possible to connect the external function section having various functions, if required, to the aforementioned blood circuit because the external connection ports are provided there in accordance with the various functions. Even in a case of an apparatus needing a complex extacorporeal circulation circuit, such as a blood component separation apparatus using the double filtration or the single needle type recirculation blood plasma collection method, no cumbersome operation is necessary upon the assembly of the apparatus and a circuit connection error can be eliminated according to the present invention.

The blood circuit of a multi-layered structure as has already been set forth above can also obtain various advantages, such as performing more saving in the amount of priming liquid than that in the conventional apparatus.

For the conventional apparatus, individual component parts are independently sterilized prior to using the apparatus. According to the present invention, a sterilizing operation can be simplified because the main component parts are built up as a multi-layered structure and hence less component parts are used for sterilization. Further, there is a high possibility that various germs will be deposited on the sterilized component parts upon assembly of the conventional apparatus. The apparatus of the present invention can readily be assembled after sterilization, thus avoiding the deposition of the germs on the component parts.

BRIEF DESCRIPTION OF DRAWINGS

FIGS. 4A and 4B and FIGS. 5A and 5B are views showing other component parts of the blood component separation apparatus shown in FIG. 1;

FIG. 6 is a cross-sectional view as taken along line VI—VI in FIG. 1;

FIGS. 7 and 8 are cross-sectional views as taken along lines VII—VII and VIII—VIII in FIG. 2;

FIGS. 9A and 9B are views showing a blood component separation filter;

BEST MODE OF CARRYING OUT THE INVENTION

Figure 1:
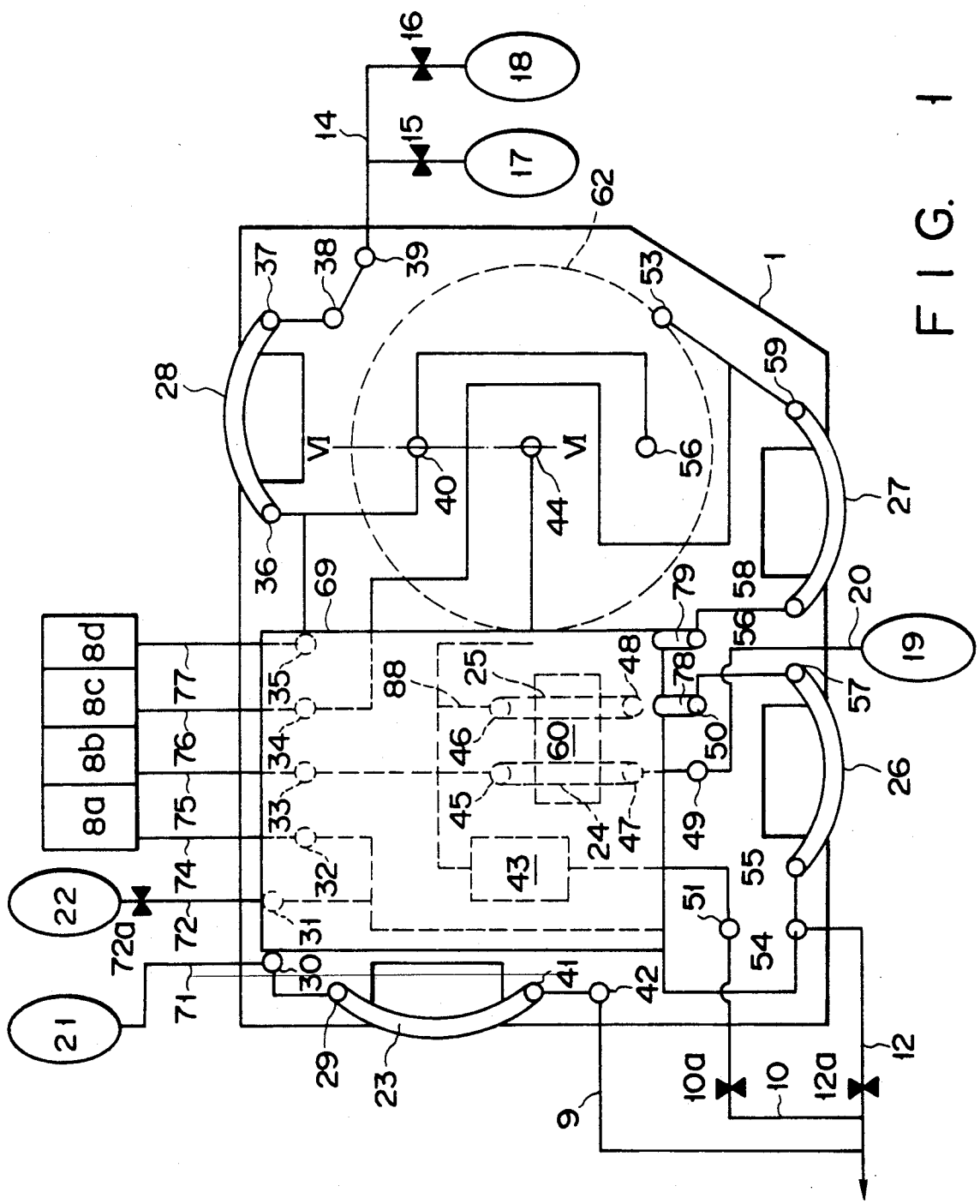
FIG. 1 is a plan view showing a blood component separation apparatus according to one embodiment of the present invention.
Figure 2:
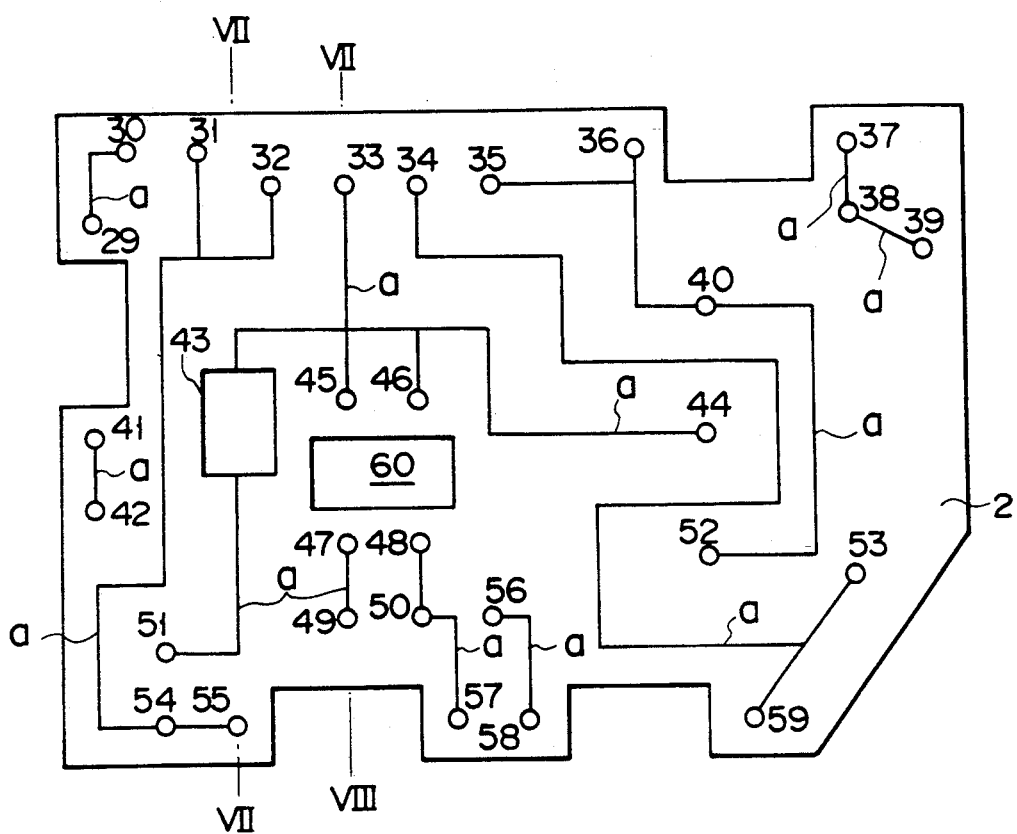
FIGS. 2 and 3 are plan views showing the component parts of the blood component separation apparatus shown in FIG. 1.
Figure 3:
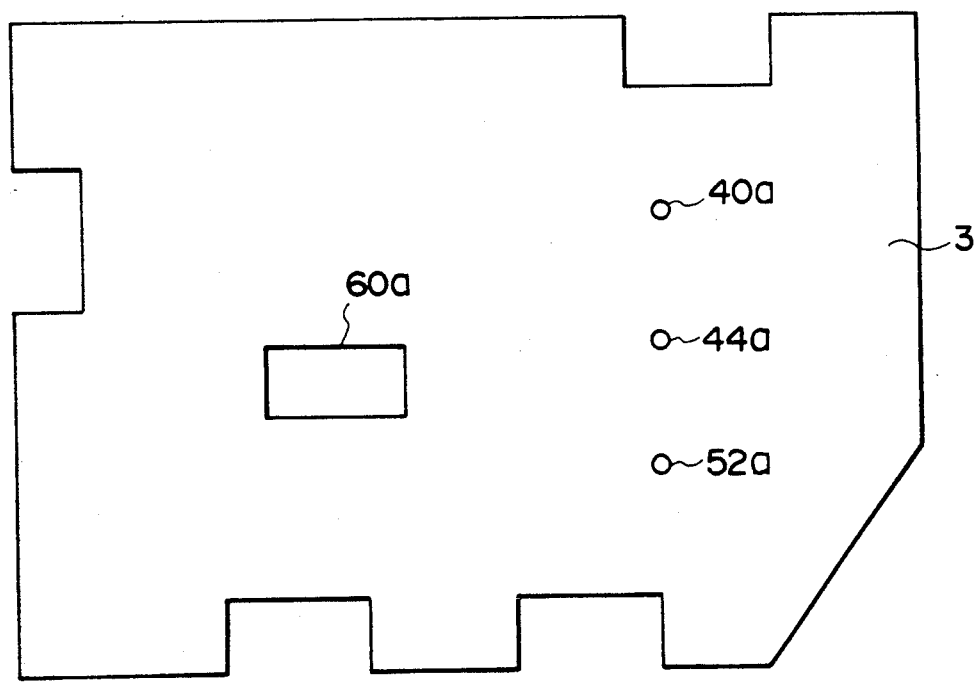

FIGS. 1 to 9 show an embodiment of the present invention which is applied to a single-needle type recirculation plasma separation apparatus. FIG. 1 is a plan view showing a whole arrangement of the present embodiment; FIG. 6 is a cross-sectional view taken along line VI—VI in FIG. 1; and FIGS. 2 to 5 and 9 are views showing component parts of the arrangement as set forth above.

In FIG. 1, reference numeral 1 shows an assembly including a blood circuit and bubble trap and a filter section. The assembly 1 comprises a four-layered structure composed of a first plate-like member 2 shown in FIG. 2, a second plate-like member 3 shown in FIG. 3, a third plate-like member 5 shown in FIGS. 5A and 5B and a fourth plate-like member 4 shown in FIGS. 4A and 4B—see FIG. 6. FIGS. 7 and 8 are cross-sectional views showing arrangements taken along line VII—VII and along line VIII—VIII in FIG. 2, respectively.

The first plate-like member 2 includes, as shown in FIG. 1, a greater number of connection ports 29 to 42 and 44 to 59 as through-holes or recesses in which case the connection ports 40, 44, are recesses. The plate-like member 2 also includes an opening 60 and a recess 44. Grooves a connect the connection port to the corresponding connection port and the external connection port to the recess 43 and provide a pattern defining a predetermined blood circuit.

As the first plate-member, use can be made of a desired molding obtained by forming a relatively rigid synthetic resin by, for example, an injection-, extrusion-, vacuum- and compressed-air molding method in which case the synthetic resin may be of such a type as to be used, for example, for medical application. The aforementioned synthetic resin includes polyvinyl chloride, polycarbonate, acrylonitrile-butadiene-styrene copolymer, polystyrene, etc.

The second plate-like member 3 includes opening 60a, ports 40a, 44a and 52a which are so provided as to correspond to the opening 60, ports 40, 44 and 52, respectively. The first plate-like member 2 and second plate-like member 3 are attached to each other in a superimposed fashion to provide clearances at the locations of the grooves a and recess 43. The grooves a provide blood circuits and the recess 43 provides a bubble trap. The openings 40a, 44a provide a connection port for a blood circuit formed between the third and fourth plate-like members 5 and 4. The openings 60, 60a serve as a through-hole for inserting, for example, a circuit clamp, as set forth in FIG. 11.

The medical synthetic resin can be formed into a desired shape for the second plate-like member 3 as in the case of the first plate-like member. In this case, the synthetic resin is of such a type that it can be bonded to the first plate-like member by a suitable method, such as a high frequency fusion and an ultrasonic fusion method as well as by a solvent, bonding agent, etc. As the synthetic resin, use can be made of, for example, polyvinyl chloride, polycarbonate polypropylene, acrylonitrile-butadiene-styrene copolymer, polystyrene, ethylene-vinylacetate copolymer, polyurethane, synthetic rubber and silicone rubber.

FIG. 5A is a plan view showing the third plate-like member and FIG. 5B is a cross-sectional view showing the third plate-like member of FIG. 5A. As shown in FIG. 5B, the third plate-like member 5 has a plate-like configuration with a flange 5a and connection ports 64 to 67 on the bottom. These connection ports are connected to the corresponding connection ports 40, 44, 52 and 53 of the first plate-like member. The third plate-like member 5 can be formed, by a similar method, into a desired configuration with the use of the same synthetic resin as the first plate-like member 2.

FIG. 4A is a plan view showing the fourth plate-like member and FIG. 4B is a cross-sectional view showing the plate-like member of FIG. 4A. As shown in these Figures, the fourth plate-like member 4 has a disc-like configuration. The fourth plate-like member 4 is attached to the third plate-like member 5 at a location of a flange 5a of the latter member. The fourth plate-like member 4 can be formed by a similar method into a desired configuration with the use of the same method as set forth above.

A flat film stacking type filter 62 as shown in FIGS. 9A and 9B is disposed between the third and fourth plate-like members 5 and 4, FIGS. 9A and 9B being a plan view and cross-sectional view, respectively. The filter 62 is composed of a large number of microporous films 62b which have a fluid passage 62a as shown in FIGS. 9A and 9B. In this way, the blood circuit is three-dimensionally constructed including the filter section.

As shown in FIG. 1, a pump tube 23 connects the connection port 29 to the connection port 41, a pump tube 26 connects the connection port 55 to the connection port 57, a pump tube 27 connects the connection port 58 to the connection port 59 and a pump tube 28 connects the connection port 36 to the connection port 37. The first and second plate-like members 2 and 3 have cutouts corresponding to the aforementioned connection ports. A roller pump as shown in FIG. 10 is incorporated into the cutouts.

Figure 10:
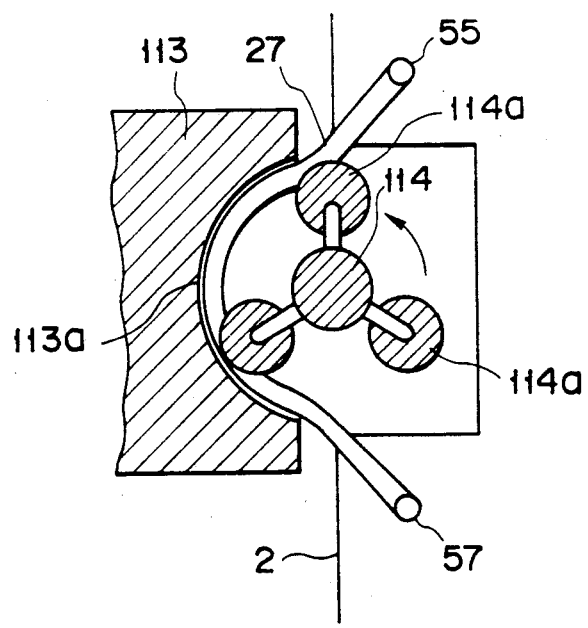
FIG. 10 is an explanatory view for explaining the operation of a roller pump.

In FIG. 10, reference numeral 113 shows a tube fixing member. The tube fixing member 113 has a circular fixing surface 113 along which the pump tube 27 is fitted in place. A rotor 114 is located opposite to the circular fixing surface 113a and has three rollers 114a relative to the surface 113a. The rotor 114 is rotated in a predetermined direction, while allowing the rollers 114a to be pressed against the pump tube 27, so that a liquid, such as the blood, is driven in a predetermined direction.

Figure 11:
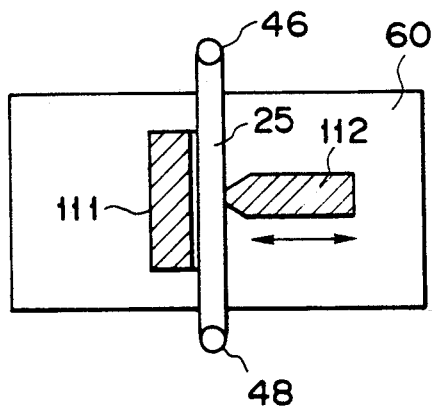
FIG. 11 is an explanatory view showing a blood circuit clamp.

As shown in FIG. 1, the connection tube 24 connects the connection port 45 to the connection port 47 and the connection tube 25 connects the connection port 46 to the connection port 48. The through-holes (the openings 60, 60a) are formed relative to these connection ports. A circuit clamp as shown in FIG. 11 is incorporated into the through-hole. As shown in FIG. 11, the circuit clamp thus incorporated comprises a fixed member 111 and a pushing member 112 which is reciprocable in a direction orthogonal to the surface of the fixed member 111 as indicated by an arrow in FIG. 11. The connection tube 25 is attached to the surface of the fixed member 111 and its fluid passage is blocked by pressing the pushing member against the tube. This structure has an advantage in that it is possible to readily mount the circuit clamp in place in the associated structure.

The other connection ports in the first plate-like member are connected to the external function sections as already set out above. For example, a blood storage container 69 is connected to connection ports 78 and 79. As the blood storage container 69 use is made of a vinyl chloride bag. This bag is placed on the layered structure as shown in FIG. 1. A connection port 30 is connected to an ACD container 21 via a passage line 71 and the connection port 31 is connected by a passage line 72 to a physiological salt solution container 22 via a valve 72a. The connection port 32 is connected by a passage line 74 to a venous pressure monitor 8a, the connection port 33 is connected by a passage line 75 to an output pressure monitor 8b, the connection port 34 is connected by a passage line 76 to an input pressure monitor 8c, and the connection port 35 is connected by a passage line 77 to a blood plasma monitor 8d. Further, the connection port 42 is connected to an ACD mixing passage line 9, the connection port 51 is connected to a blood return passage line 10, and the connection port 54 is connected to a blood collection passage line 12. A valve 10a and valve 12a are provided on the blood return passage line 10 and blood collection passage line 12, respectively. The connection port 49 is connected to a spent-liquid container 19 via a passage line 20. The connection port 39 is connected respectively through a valve 15 and valve 16 to a spent blood plasma container 17 and blood plasma collection container 18 by means of a blood plasma passage line 14. The connection ports 50 and 56 are connected to the blood storage container 69 respectively through the connection tubes 78 and 79.

Figure 12:
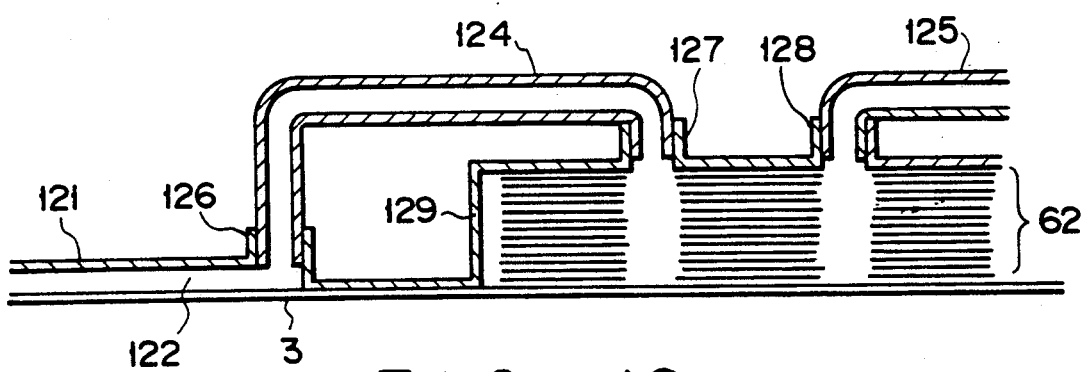
FIG. 12 is a cross-sectional view showing part of a blood component separation apparatus according to another embodiment of the present invention.

The filter 62 can be incorporated into the layered structure not only by the aforementioned method but also by other proper methods. As shown in FIG. 12, for example, use may be made of, in place of the third and fourth plate-like members 5 and 4, a plate-like unit 121 defining connection ports 126, 127 and 128, a groove 122 for defining a blood passage and a recess 129 for a filter housing. As shown in FIG. 12, the plate-like unit 121 is attached directly to a second plate-like member 3 to define a blood circuit 122 and the aforementioned filter housing 129. The filter 62 is held within the housing 129 and a communication tube 124 connects the connection port 126 to the connection port 127. The connection port 128 is connected by a communication tube 125 to a corresponding connection port. In this way, the blood circuit including the filter section can be three-dimensionally formed, as shown in FIG. 12, in the same way as that in FIG. 6 on the blood circuit which is defined by the first and second plate-like members 3 and 4. It is possible to stack blood storage containers 69 (FIG. 1) as an integral unit. In the structure as shown in FIG. 12, therefore, those connection ports which are formed on the second plate member 3 are arranged in a different way from that shown in FIG. 3.

A way of separating a plasma component from the collected blood on the blood component separation apparatus of the embodiment of FIG. 1 will be explained below. The operation process is performed in an order of a prime washing, a blood priming, a blood plasma collection, blood returning and washing step.

Prime Washing

First, the valves 72a and 12a are opened to flow a physiological saline into the passage line 72, passage line across the connection port 31 and 54, and passage line 12. The physiological saline is introduced into the blood storage container 69 via a passage between the connection ports 54 and 55 and that between the connection ports 57 and 50 by rotating a roller pump of the communication tube 26 with the valve 12a and communication tube 25 closed. At the same time, the roller pump of the communication tube 27 is rotated with the valve 10a and communication tube 24 opened and closed, respectively. That liquid supply speed is set at the same rate as that of the communication tube 26. In this way, a physiological saline is introduced into the separation filter 62 with the use of the passage between the connection ports 56 and 58 and that between the connection ports 59 and 53. The priming of the filter 62 is carried out with the passage line (including the valve trap 43) between the connection ports 44 and 51 and passage line 10.

The roller pump of the communication tube 28 is rotated with the valves 15 and 16 opened and closed, respectively. By the passage line through the connection ports 52, 40, 36, 37, 38 and 39, the physiological saline which has been filtered by the filter 62 is discharged followed by the priming of the filterate circuit.

Finally, the priming of the ADC container 21 is carried out by the passage line 71 connected to ADC container, passage line connected between the connection ports 30, 29 and 41, 42, and passage line 9. The priming operation is performed by rotating the roller pumps of the communication tubes 26, 27 and 28 with the valves 72a, 10a and communication tube 25 closed and the roller pumps of the communication tubes 26, 27 and 28 stopped. After the priming of the ACD line is completed, the roller pump of the communication tube 23 is stopped.

Blood Priming

A blood donor is intravenously injected by a syringe needle for blood collection. Then the roller pumps of the communication tubes 26 and 27 are rotated at a flow speed of 50 ml/min. with the valves 12a, 15 and communication tube 24 opened. In this way, the circuit is filled with the blood and stored in the blood storage container 69.

At the same time, the roller pump of the communication tube is rotated at a liquid supply speed of 10 ml/min. and the roller pump of the communication tube 23 is rotated. Normally, the roller pump of the communication tube 23 is rotated at a speed of a tenth that of the roller pump of the communication tube 26, that is, at the liquid supply speed of 5 ml/min. By so doing, an ACD solution is mixed in the blood collected.

The communication tube 25 is opened after two minutes and the communication tube 25 is opened. After the lapse of one minute, the roller pumps of the communication tubes 23 and 26 are stopped and the rotation speed of the roller pump of the communication tube 27 is raised up to a liquid supply speed of 75 ml. At the same time, the valve 12a and communication tube 25 are opened and closed, respectively, to allow the blood which is taken up in the blood storage container 69 to be returned back to the donor. At the time when the blood in the blood storage container 69 is drained, the valves 10a, 15 are closed and the communication tube 25 and valve 66 are opened so that the blood plasma collection operation may be performed.

Plasma Collection

The blood priming is followed by a blood collection and a plasma collection step through blood recirculation.

First, the roller pumps of the communication tubes 23 and 26 are rotated at liquid supply speeds of 5 ml/min. and 50 ml/min. and the roller pump of the communication tube 27 is rotated at the liquid supply speed of 75 ml/min. By so doing, the blood which is drawn from the donor passes through the filter 62 where the plasma component is taken from the blood. After the plasma taking step, the filtered blood is stored in the blood storage container 69. The blood being thus stored, together with the blood freshly drawn in, is recirculated through the filter 62 to allow the taking of the plasma from the blood to be repeated. The blood plasma component is supplied from the filter 62 into the blood plasma collection container 18 for storage. It is to be noted that, during the blood collection, the roller pump of the communication tube 28 is rotated at a liquid supply speed of 13 ml/min.

One plasma collection cycle is completed when 25 to 250 ml of blood is taken as a predetermined amount. This step is carried out by stopping the roller pumps of the communication tubes 23 and 26 and opening the valve 10a with the communication tube 25 closed. Then a blood returning cycle is performed until all the blood is run out of the blood storage container 69. During this period of time, the roller pump of the communication tube 28 is rotated at the speed of 13 ml/min.

The plasma taking and blood returning steps are repeated until the amount of blood plasma in the blood collection container 18 reaches 400 to 500 ml as a predetermined amount. When that predetermined amount of plasma component is reached, all the roller pumps are stopped with the valve 16 closed.

Blood Return and Washing

The valves 12a and 72a are closed and opened, respectively. The blood in the blood circuit is returned back to the donor by rotating the roller pumps of the communication tubes 26 and 27 at the liquid supply speed of 50 ml/min. for 1 minute.

Then the physiological saline is stored in the blood storage container 69 by rotating the roller pump of the communication tube 26 at the liquid supply speed of 50 ml/min. with the roller pump of the communication tube 27 stopped.

Then the valves 72a and 12a are closed and opened, respectively. In this way, the roller pump of the communication tube 26 is rotated, in a reverse direction, at the liquid supply speed of 50 ml/min. for 1 minute to allow the passage line 12 to be washed.

Then with the valves 10a and 12a closed, the roller pump of the communication tube 27 is rotated, in the reverse direction, at the liquid supply speed of 50 ml/min. for 10 seconds to wash the line 88, communication tube 25 and connection ports 48 and 50.

Then the communication tube 25 is closed and the valves 72a and 10a are opened. In this state, the roller pumps of the communication tubes 26 and 27 are rotated, in the normal direction, at the liquid supply speed of 50 ml/min. for 1 minute to allow the filter 62 to be washed.

Finally, the blood plasma collection operation is ended by withdrawing the syringe needle out of the donor.

We claim:

1. A blood component separation apparatus comprising:
   at least three plate-like members arranged in a stacked fashion;
   a blood circulation circuit comprising at least two layers which are arranged between associated plate-like members and at least partly defined by grooves in said plate-like members;
   a filter housing formed as a part of blood passages in the blood circulation circuit;
   a blood component separation filter mounted in the filter housing;
   a plurality of connection ports provided in the plate-like members to allow communication with the blood circulation circuit;
   communication tubes mounted in the blood circulation circuit to place part of the connection ports in communication with associated ports, the communication tubes including means for controlling fluid communication in the blood circulation circuit; and
   an external function section connected to corresponding connection ports.

2. The blood component separation apparatus according to claim 1, wherein an opening is provided in at least two of said at least three plate-like members at a location not hampering the function of said blood circulation circuit, said communication tubes are provided across the opening, and a clamping member is provided at the opening to control the closing and opening of the communication tube.

3. The blood component separation apparatus according to claim 1, wherein, at a marginal position not hampering the function of said blood circulation circuit, cutouts are so provided as to penetrate at least two of said at least three plate-like members with said communication tube arranged across the cutouts, and a roller pump is mounted in the cutout with the communication tube located relative to the roller pump.

4. The blood component separation apparatus according to claim 1, wherein said blood circulation circuit has a valve trap.

5. The blood component separation apparatus according to claim 1, wherein said blood circulation circuit has a pressure monitoring circuit.

6. The blood component separation apparatus according to claim 1, wherein said blood circulation circuit has a circuit closing site.

7. The blood component separation apparatus according to claim 1, wherein said blood circulation circuit has a housing section for a filter mechanism.

8. The blood component separation apparatus according to claim 1, wherein said blood circulation circuit has a liquid level detection section.

9. The blood component separation apparatus according to claim 1, wherein said blood circulation circuit has a hemolysis detection section.

10. The blood component separation apparatus according to claim 1, wherein said blood circulation circuit has a blood storage container.

11. The blood component separation apparatus according to claim 1, wherein said blood circulation circuit has a sample collection inlet.

12. The blood component separation apparatus according to claim 1, wherein said external function section has a blood discharging passage line.

13. The blood component separation apparatus according to claim 1, wherein said external function section has a blood return passage line.

14. The blood component separation apparatus according to claim 1, wherein said external function section has an anti-coagulant mixing passage line.

15. The blood component separation apparatus according to claim 1, wherein said external function section has a pressure-monitoring port connection line.

16. The blood component separation apparatus according to claim 1, wherein said external function section has a physiological saline passage line.

17. The blood component separation apparatus according to claim 16, wherein said external function section has an anti-coagulant mixing passage line.

18. The blood component separation apparatus according to claim 1, wherein said external function section has a blood component collection container.

19. The blood component separation apparatus according to claim 1, wherein said external function section has a blood storage container.

20. The blood component separation apparatus according to claim 1, wherein said external function section has a blood component discharging container.

21. The blood component separation apparatus according to claim 1, wherein said external function section has a liquid medicine container connection passage line.

22. The blood component separation apparatus according to claim 1, wherein said communication tubes comprise a pump tube with a roller pump set in place.

23. The blood component separation apparatus according to claim 1, wherein said communication tubes are set relative to an external tube closing unit to provide a circuit closing site.

24. The blood component separation apparatus according to claim 1, wherein a filter for blood component separation comprises a flat type filter having a layered structure.

* * * * *